United States Patent [19]

Guntaka

[11] Patent Number: 4,518,690

[45] Date of Patent: May 21, 1985

[54] **DNA PROMOTER SEQUENCE OF AVIAN TUMOR VIRUS AND USE THEREOF FOR ENHANCED GENE EXPRESSION IN *E. COLI***

[75] Inventor: Ramareddy V. Guntaka, Teaneck, N.J.

[73] Assignee: Research Corporation, New York, N.Y.

[21] Appl. No.: 424,631

[22] Filed: Sep. 27, 1982

Related U.S. Application Data

[63] Continuation of Ser. No. 145,390, Apr. 30, 1982, abandoned.

[51] Int. Cl.$^3$ .................. C12P 21/04; C12P 21/00; C12P 21/02; C12N 15/00; C12N 1/20; C12N 1/00; C07H 15/12

[52] U.S. Cl. .................................. 435/71; 435/68; 435/70; 435/172.3; 435/253; 435/317; 536/27; 935/8; 935/32; 935/73

[58] Field of Search ............... 435/172, 253, 317, 68, 435/70, 71; 536/27

[56] References Cited

PUBLICATIONS

Backman et al., Cell, vol. 13, pp. 65–71, (Jan. 1978).

Backman et al., PNAS USA, vol. 73, pp. 4174–4178, (Nov. 1976).

Goeddel et al., Native, vol. 281, pp. 544–548, (Oct. 18, 1979).

R. V. Guntake et al., "Binding of *Escherichia coli* RNA Polymerase to a Specific Site Located Near the 3′-End of the Avian Sarcoma Virus Genome", *Biochimica et Biophysica Acta*, 607, (1980), 457–469.

R. V. Guntake et al., "Cloning of Avian Tumor Virus DNA Fragments in Plasmid pBR322: Evidence for Efficient Transcription in *E. coli* from a Virus-coded Promoter", *Gene*, 12, (1980), 113–121.

S. A. Mitsialis et al., "An Avian Tumor Virus Promoter Directs Expression of Plasmid Genes in *Escherichia coli*", *Gene*, 0(1981), Gene 504.

Wang, L., The Gene Order of Avian RNA Tumor Viruses Derived from Biochemical Analyses of Deletion Mutants and Viral Recombinants, *Ann. Rev. Microbiol.*, 32, 1978, 561–592.

Hsu, T. et al., Analysis of Unintegrated Avian RNA Tumor Virus Double-Stranded DNA Intermediates, *Journal of Virology*, 28, Dec. 1978, 810–818.

Shank, P. R. et al., Mapping Unintegrated Avian Sarcoma Virus DNA: Termini of Linear DNA Bear 300 Nucleotides Present Once or Twice in Two Species of Circular DNA, *Cell*, 15, Dec. 1978, 1383–1395.

Hughes, S. H. et al., Proviruses of Avian Sarcoma Virus Are Terminally Redundant, Co-extensive with Unintegrated Linear DNA and Integrated at Many Sites, *Cell*, 15, Dec. 1978, 1397–1410.

Sabran, J. L. et al., Analysis of Integrated RNA Tumor Virus DNA in Transformed Chicken, Duck, and Quail Fibroblasts, *Journal of Virology*, 29, Jan. 1979, 170–178.

Rymo, L. et al., In Vitro Synthesis of Virous Sarcoma Virus-Specific RNA is Catalyzed by a DNA-Dependent RNA Polymerase, *Proc. Nat. Acad. Sci. USA*, 71, Jul. 1974, 2782–2786.

(List continued on next page.)

*Primary Examiner*—Alvin E. Tanenholtz
*Attorney, Agent, or Firm*—Scully, Scott, Murphy & Presser

[57] ABSTRACT

A molecule of double-stranded DNA having a length of about 35 base pairs has been removed from the first 150 base pairs at the 3′-end of Avian sarcoma viral DNA. This molecule binds to *E. coli* RNA polymerase and acts as a promoter of gene expression in *E. coli*. *E. coli* cells have been transformed with cloning vehicles which include this promoter DNA molecule and enhanced gene expression has been observed in the transformed cells. By including the promoter DNA molecule in cloning vehicles along with a gene associated with the production of a desired chemical product, such as proinsulin, the polypeptide A or B chains of insulin, the polypeptide portion of interferon, a growth hormone, an enzyme or an antibody, it will be possible to obtain enhanced production of such desired chemical products.

25 Claims, 6 Drawing Figures

PUBLICATIONS

Hayward, W. S., Size and Genetic Content of Viral RNAs in Avian Oncovirus-Infected Cells, *Journal of Virology*, 24, Oct. 1977, 47-63.

Heyden, B. et al., Letters To Nature, Single RNA Polymerase Binding Site Isolated, *Nature New Biology*, 240, Nov. 1972, 9-12.

Pribinow, D., Bacteriophage T7 Early Promoters: Nucleotide Sequences of Two RNA Polymerase Binding Sites, *J. Mol. Biol.*, 99, 419-443, (1975).

Maniatis, T. et al., Recognition Sequences of Repressor and Polymerase in the Operators of Bacteriophage Lambda, *Cell*, 5, Jun. 1975, 109-113.

Brown, K. D. et al., RNA Polymerase Interaction at the Promoter-Operator Region of the Tryptophan Operon of *Escherichia coli* and *Salmonella typhimurium*, *J. Mol. Biol.*, 121, (1978), 153-177.

Doi, R. H., Role of Ribonucleic Acid Polymerase in Gene Selection in Procaryotes, *Bacteriological Reviews*, 41, Sep. 1977, 568-594.

Vogt, P. K., Genetics of RNA Tumor Viruses, *Comprehensive Virology*, (Frankel, H. et al., editors), vol. 9, 341-455, Plenum Press, New York, (1977).

Jacquet, M. et al., The In Vitro Synthesis of Avian Myeloblastosis Viral RNA Sequences, *Proc. Nat. Acad. Sci. USA*, 71, Aug. 1974, 3045-3049.

Lescure, B. et al., Transcription of Polyoma Virus DNA In Vitro, III. Localization of Calf Thymus RNA Polymerase II Binding Sites, *J. Mol. Biol.*, 124, 1978, 87-96.

Taylor, J. M. et al., Avian RNA Tumor Virus DNA Before and After Integration into the Host Genome, Cold Spring Harbor Symposium, *Quant. Biol.*, 43, (1979), 865-867.

Tsichlis, P. N. et al., Recombinants Between Endogenous and Exogenous Avian Tumor Viruses: Role of the C Region and Other Portions of the Genome in the Control of Replication and Transformation, *Journal of Virology*, 33, Jan. 1980, 238-249.

Gilbert, W., "Starting and Stopping Sequences for the RNA Polymerase, Cold Spring Harbor Symp., Quant. Biol., 41: 193-205, (1976).

Monroy, G. et al., "AMV RNA Transcription in Cell-free Systems and Properties of In Vitro Chromatin-directed RNA Synthetis", Cold Spring Harbor Symp., Quant. Biol., 39: 1033-1041, (1974).

DNA PROMOTER SEQUENCE OF AVIAN TUMOR VIRUS AND USE THEREOF FOR ENHANCED GENE EXPRESSION IN *E. COLI*

The invention described herein was made in the course of work under Contract Number N01 CP71055 and Grant Number 1 K04 CA 00540-01 from the Department of Health, Education and Welfare.

This is a continuation, of application Ser. No. 145,390 filed Apr. 30, 1982, and now abandoned.

FIELD OF THE INVENTION

This invention generally concerns the use of recombinant DNA technology to direct or otherwise control gene expression in bacterial cells, specifically, in *Escherichia coli*. It is particularly directed to increasing the production of desired proteinaceous and other materials by enhancing the expression of genes which are directly or indirectly associated therewith.

BACKGROUND OF THE INVENTION

RNA tumor viruses typically contain an RNA genome of about 10.000 nucleotides (Bishop, J. M., Ann. Rev. Biochem., 47:35-88 (1978)). The structure of the RNA is unique in several aspects (Wang, L. H., Ann. Rev. Microbiol., 32:61-92 (1978)). Apart from three well defined structural genes, a sequence of about 600 nucleotides, which is generally referred to as C or common region, is present in almost all RNA tumor viruses studied to date. (Bishop, J. M., Ann. Rev. Biochem., 47:35-88 (1978); Wang, L. H., Ann. Rev. Microbiol., 32:61-92 (1978)). This sequence, whose function is not known, is located at the 3'-end of the RNA immediately adjacent to a Poly A sequence (Wang, L. H., Ann. Rev. Microbiol., 32:61-92 (1978). When the RNA is copied into double-stranded DNA by the virion-associated reverse transcriptase, a portion (approximately 300 base pairs) of the C region is repeated in the DNA to form two large terminal repeats (LTR). (Hsu, T. W., Sabran, J. L., Mark, G. E., Guntaka, R. V. and Taylor, J. M., J. Virol., 28:810-818 (1978); Shank, P. R., Hughes, S. H., Kung, H. J., Majors, J. E., Quintrell, N., Guntaka, R. V., Bishop, J. M. and Varmus, H. E., Cell, 15:1383-1895 (1978)). Upon integration into a host cell genome the same order of the linear DNA, including the large terminal repeats, is maintained (Hughes, S. H., Shank, P. R., Spector, D. H., Kung, H. J., Bishop, J. M., Varmus, H. E., Vogt, P. K. and Breitman, M. L., Cell, 15:1397-1410 (1978); Sabran, J. L., Hsu, T. W., Yeater, C., Kaji, A., Mason, W. S. and Taylor, J. M., J. Virol, 29:170-178 (1979)). In other words, the large terminal repeats are flanked by the host cellular sequences and the arrangement of the integrated viral genome is colinear with unintegrated linear viral DNA.

In virus-infected cells, the host cellular RNA polymerase II transcribes viral RNA so that as much as 5-10% ($5 \times 10^3$ to $10 \times 10^3$ copies per cell) of the total poly A-containing RNA in the cell is virus-specific. (Rymo, L., Parsons, J. T., Coffin, J. M. and Weissman, C., Proc. Natl. Acad. Sci. USA 71:2782-2786 (1974); Hayward, W. S., J. Virol., 24:47-63 (1977)). This observation suggests the presence of some unusual structural feature or features in the DNA of RNA tumor viruses which allow selective binding of RNA polymerase. One possibility is that a strong promoter is present in the large terminal repeat of viral DNA.

In several systems, including bacteriophages fd (Heyden, B., Nusslein, C. and Schaller, H., Nature New Biol. 96: 9-12 (1972)); T7 (Pribnow, D. J., Mol. Biol. 99: 419-443 (1975)) and λ (Maniatis, T., Ptashne, M., Backman, K., Kleid, D., Flashman, S., Jeffrey, A. and Maurer, R., Cell 5: 109-113 (1975)) and bacteria (Gilbert, W., Cold Spring Harbor Symp. Quant. Biol. 41: 193-205 (1976); Brown, K. D., Bennet, G. N., Lee, F., Schweingruber, M. E. and Yanofsky, C., J. Mol. Biol. 121: 153-177 (1978)), the promoter sites have been isolated from the DNA are sequenced. This has been achieved by using *Escherichia coli* RNA polymerase which recognizes and tightly binds to a promoter sequence on the DNA and renders it resistant to subsequent digestion by deoxyribonuclease. In all the cases studied so far the polymerase protects from nuclease digestion a fragment about 35-40 base pairs long. Nucleotide sequence analysis has revealed a greater degree of sequence conservation among various promoters (Doi, R. H., Bact. Rev. 41: 568-594 (1977)).

There are several subgroups of avian tumor viruses (Vogt, P. K., in *Comprehensive Virology* (Frankel, H., Conrad, R. R. and Wagner, R. F., eds.), Vol. 9, pp. 341-455, Plenum Press, New York (1977)). In these viruses at least portions of the C region appear to be well conserved among several exogenous viruses (Vogt, P. K., in *Comprehensive Virology* (Frankel, H., Conrad, R. R. and Wagner, R. F., eds.), Vol. 9, pp. 341-455, Plenum Press, New York (1977)). In the virus-infected cells, the host cell RNA polymerase II transcribes viral RNA as shown by the sensitivity of transcriptions to α-amanitin (Rymo, L., Parsons, J. T., Coffin, J. M., and Weissman, C., Proc. Natl. Acad. Sci. U.S.A. 71: 2782-2786 (1974); Jacquet, M., Groner, Y., Monroy, G. and Hurwitz, J., Proc. Natl. Acad. Sci. U.S.A. 71: 3045-3049 (1974)). Previous studies have shown that avian myeloblastosis virus specific RNA can be transcribed by *E. coli* RNA polymerase in a reconstructed chromatin system from virus infected chick cells at levels comparable to that of infected whole cells (Monroy, G., Jacquet, M., Groner, Y. and Hurwitz, J., Cold Spring Harbor Symp. Quant. Biol. 39: 1033-1041, (1974)). This suggests that *E. coli* RNA polymerase does recognize a putative promoter site and is able to transcribe viral RNA. Recently it has been shown that calf thymus RNA polymerase II recognizes and binds to polyoma DNA at the same sites as that of *E. coli* RNA polymerase (Lescure, B., Dauget, C. and Yaniv, M., J. Mol. Biol. 124: 87-96 (1978)). Therefore, studies with RNA polymerase from *E. coli* should enable one to identify the site, if it exists on the avian sarcoma virus (ASV) DNA. As set forth hereinafter, such a site in ASV DNA has been located in a region corresponding to the first 50-60 nucleotide heteropolymeric region of RNA immediately adjacent to the 3'-end poly (A) sequence. Furthermore, this RNA polymerase binding site has been shown to function as a promoter of gene expression when cloned in *E. coli*.

SUMMARY OF THE INVENTION

This invention provides a molecule of double-stranded DNA having a length of about 35 base pairs useful as a promoter of gene expression in *E. coli*. This promoter molecule has the base pair sequence which binds *E. coli* RNA polymerase and is found in the first 150 base pairs at the 3'-end of Avian sarcoma viral DNA.

A molecule which includes the promoter molecule and a gene or genes associated with the production of a desired chemical product such as a polypeptide or a compound containing a polypeptide portion may be joined to a cloning vehicle such as a plasmid or phage and inserted into a host *E. coli* cell by transformation.

*E. coli* cells which have been so transformed may then be cloned under conditions permitting enhanced gene expression and thus enhanced production of desired chemical products.

DETAILED DESCRIPTION OF THE INVENTION

Figure 1:
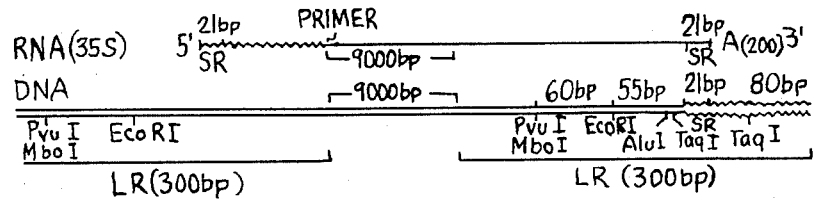
FIG. 1 Maps of ASV RNA and DNA. In the upper line the genetic map of ASV 35S RNA is given to indicate the short-terminal repeat (SR) of 21 nucleotides. The wavy line repesents the 5'-end of 101 nucleotides whose sequence is known. The lower double lines represent the DNA. DNA synthesis begins near the 5'-end of the RNA genome using tRNA$^{Trp}$ as primer, proceeds to that end and then jumps to the 3'-end of RNA where synthesis resumes. The right end of the linear DNA (wavy line) corresponds to the 5'-end 101 nucleotides of RNA. In the DNA this sequence and another 200 nucleotides of the constant region are repeated (LR). The cleavage sites for some of the restriction enzymes are also given. bp=base pairs.

A promoter of gene expression may be defined as a region or sequence along a DNA molecule at which RNA polymerase binds and initiates transcription. The existence of several promoters has been reported previously. Such promoters are of particular interest for the commercial development of processes for producing desired chemical products using recombinant DNA techniques. Although the present level of recombinant DNA technology has permitted the production of certain chemical products such as the unprocessed polypeptide portion of interferon, proinsulin and somatostatin, the yields obtained are exceedingly low. Thus, for example, *E. coli* cells which have been transformed by a plasmid carrying the gene for interferon polypeptide produce on average, only about 1–2 molecules of polypeptide. Ultimately, the commercial success of recombinant DNA will depend upon the ability to substantially improve the yields of desired products. One solution to this problem will be the use of a promoter molecule to enhance gene expression and thus production of desired product. The present invention provides a double-stranded DNA molecule useful as a promoter of gene expression in *E. coli*. This promoter molecule has a length of about 35 base pairs, binds *E. coli* RNA polymerase, and enhances the expression of genes with which it is associated. The promoter molecule has been found in the first 150 base pairs at the 3'-end of Avian sarcoma virus and may be separated therefrom. Alternatively, the promoter molecule may be independently synthesized.

Although the precise nucleotide sequence of the promoter molecule has not yet been determined, its location within the viral DNA and its length have both been established. It would thus be a matter well within the skill of those in the art to determine the precise nucleotide sequence of the promoter DNA molecule. Thus, as discussed more fully hereinafter, the promoter molecule has a length of about 35 base pairs and is found in the first 150 base pairs at the 3'-end of Avian sarcoma viral DNA or within the first 50 nucleotides (150 minus 101 nucleotide strong stop DNA) of the heteropolymeric region, that is, in the DNA corresponding to the sequence immediately adjacent to the poly (A) region of the RNA genome.

Moreover, the sequence of the first 150 nucleotides at the 3'-end of Avian sarcoma viral DNA is known. In particular, the sequence of the DNA strand complementary to the viral RNA is the following:

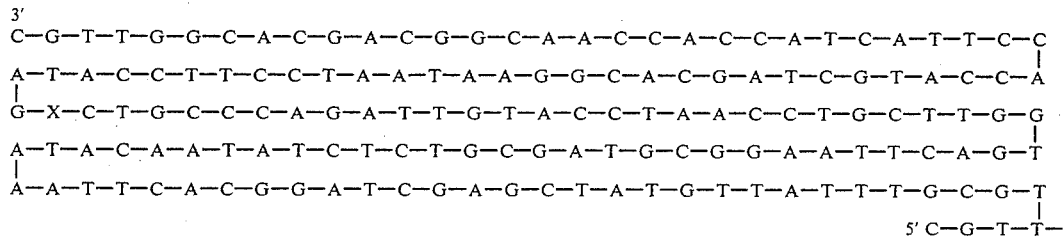

Since the second DNA strand is complementary, its sequence is known as well.

In commercial applications the promoter DNA molecule will be chemically joined to a double-stranded DNA molecule which includes at least one gene which is associated with the production of a desired chemical product, likely a gene which does not naturally occur in the same molecular as the promoter. Such chemical linkage may be obtained, for example, by means of a ligase. In the resulting double-stranded DNA molecule, the promoter and gene or genes associated with the production of desired chemical products may be contiguous or noncontiguous, limited only by the ability of the promoter to effect enhanced transcription and expressions of the gene or genes.

Typically, the desired chemical product will be a polypeptide or a compound containing a polypeptide portion and the gene will directly code for its production. However, it is within the scope of this invention for the desired chemical product to be produced by the gene or to be produced by a reaction in which the polypeptide has an essential role. Examples of desired chemical products which may be produced in enhanced amounts using the invention are insulin, the polypeptide A and B chains of insulin, proinsulin, interferon, the polypeptide portion of interferon, growth hormones such as somatostatin, enzymes and antibodies.

A molecule which includes the promoter molecule and a gene associated with production of a desired chemical product will be chemically joined, e.g., by a ligase, to a molecule useful as a cloning vehicle such as plasmid, phage or viral DNA to form a hybrid or modified cloning vehicle which retains the capacity to transform host bacterial cells, specifically, E. coli cells. This hybrid or modified cloning vehicle will then be used to transform E. coli cells according to transformation techniques well known to those skilled in the art. In this way, genes associated with production of desired chemical products will be inserted into host E. coli cells which will be cloned and grown in culture under suitable conditions permitting gene expression and production of desired products in enhanced yields as compared with the yields obtainable without the promoter molecule. The chemical product so produced may then be recovered from the bacterial cells, and if desired, further isolated or purified according to well known techniques. It will thus be possible to obtain enhanced production of numerous chemical products such as the polypeptide A and B chains of insulin which may then be assembled and joined by disulfide bonds to form active insulin.

As discussed previously the promoter molecular may be obtained from Avian tumor viral DNA or chemical synthesis. Thus, Avian tumor viral DNA may be admixed with RNA polymerase under conditions permitting binding of the polymerase to that portion of the Avian tumor viral DNA which is the promoter molecule. The resulting bound complex may then be contacted with an enzyme which cleaves only viral DNA which is not bound to the polymerase. The complex of uncleaved viral DNA and polymerase may then be recovered, separated into viral DNA and polymerase, and the uncleaved DNA which is the promoter molecular recovered, and if desired, further purified or isolated. Alternatively, a single-stranded DNA molecule having the nucleotide sequence complementary to Avian sarcoma viral DNA may be prepared either by assembling smaller nucleotide units of correct sequence or by translation of viral RNA. A second single-stranded DNA molecule may then be formed having the nucleotide sequence complementary to the first DNA molecule. From the two single-stranded DNA molecules, a double-stranded DNA molecule may be formed by known techniques. This double-stranded DNA may then be admixed with E. coli RNA polymerase under conditions which result in formation of a complex, unbound DNA cleaved or otherwise cut and removed, and uncleaved or uncut DNA which is the promoter molecule recovered.

Finally, if the precise sequence of the promoter molecule is determined, still other approaches to chemical synthesis may be employed.

The following details of experiments carried out to identify, isolate and utilize the promoter molecule are set forth to aid in a better understanding of the present invention, but are not intended in any way to limit the scope thereof as set forth in the preceding description and in the claims which follow.

EXPERIMENTAL RESULTS

FIRST SERIES OF EXPERIMENTS

RNA polymerase binding site in ASV DNA

The genetic map of avian tumor virus genome, a 35 S RNA, is known. (Bishop, J. M., Ann. Rev. Biochem. 47: 35–88 (1978)). Besides the structural genes, most of the avian retroviruses possess a nucleotide sequence of 600–700 nucleotides immediately adjacent to the poly(A). This region is generally referred to as constant or common or C region. (See FIG. 1) If avian tumor viral RNA has a nucleotide sequence corresponding to a RNA polymerase binding site, then reverse transcription of virion RNA to DNA should generate the same site in viral DNA. Since the viral DNA genome has a terminal repeat of about 300 base pairs, if the binding sequence lies in this repeat, then double-stranded DNA synthesized in the virion which lacks the repeat should have one site in its constant region. (LR in FIG. 1) Therefore, double-stranded DNA was synthesized using high concentrations of deoxyribonucleoside triphosphates, one of which is labeled with $^{32}P$ or $^{3}H$, in an endogeneous reverse transcriptase reaction and the product analyzed in a velocity sucrose gradient. The results showed that the majority of the product sedimented at 7 to 9 S which corresponds to a size of 800 to 1000 base pairs. Treatment of the 7 to 9 S and 12 to 15 S viral DNA with single-stranded specific S1 nuclease indicated that more than 85% of the 7 to 9 S and 80% of the 12 to 15 S is double-stranded. The proportion of large DNA is very small, (5-6%). Since the polarity of the RNA genome dictates that the DNA synthesis which is initiated at the 5'-end of the genome has to continue elongating from the 3'-end of the RNA, a predominant fraction of the 7 to 9 S DNA should represent the C region. This was confirmed by direct hybridization with purified 3' poly(A)-containing 10 S virion RNA.

Pooled viral DNA from the two size classes was assayed for binding sites by incubating with the holoenzyme of E. coli RNA polymerase. In both cases, less than 0.2% of the total input radioactivity is nuclease resistant in the absence of RNA polymerase. In the presence of 20 μg/ml RNA polymerase about 1.3% of the large DNA and 5 to 6% of the small DNA are nuclease resistant. (See Table 1) Slightly higher yields of protected DNA have been consistently observed at 0.05 M KCl than at 0.12 or 0.3 M KCl. This may be due to some nonspecific binding of RNA polymerase to DNA at the lower salt concentration. (Chamberlin, M. J., Ann. Rev. Biochem. 43: 721–775 (1974)). Inclusion of GTP or ATP in the reaction has slightly enhanced this protection at 0.3 M CKl, probably by stabilizing the initiation complexes as shown for other RNA polymerase binding sites. (Heyden, B., Nusslein, C. and Schaller, H., Nature New Biol. 96: 9–12 (1972)). Addition of the remaining two ribonucleoside triphosphates (UTP and CTP) has reduced this protection to about 20–40% that of the normal binding indicating that the polymerase has moved away from the binding site, presumably as a result of initiation of RNA transcripts (Table 1).

TABLE 1

DEMONSTRATION OF E. COLI RNA POLYMERASE BINDING ASV DNA
$^{32}$P- or $^{3}$H-labeled DNA of 7–9 S was synthesized and assayed for RNA polymerase binding as described in Materials and Methods. The percentage DNA protected by RNA polymerase from DNAase is given.

| Reaction conditions | RNA polymerase protected ASV DNA (% of total cpm) |
|---|---|
| Standard (0.05 M KCl)* | 8.8 |
| Standard (0.05 M KCl)* + ATP and GTP | 6.0 |
| Standard (0.05 M KCl)* + 4XTP | 1.9 |
| Standard (0.12 M KCl) | 5.0 |
| Standard (0.12 M KCl) + ATP and GTP | 5.7 |
| Standard (0.12 M KCl) + 4 XTP | 2.5 |
| Standard (0.3 M KCl) | 4.2 |
| Standard (0.3 M KCl) + ATP and GTP | 6.1 |
| Standard (0.12 M KCl)** | 1.3 |
| Standard (0.12 M KCl)** | 1.7 |

*These reactions were carried out using the 600 base pair DNA isolated as described in Methods and Materials.
**These reactions were carried out with 12–15S DNA (pool 1).

These results are in good agreement with those observed for other promoters (Heyden B., Nusslein, C. and Schaller, H. Nature New Bio. 96: 9–12 (1972); Pribnow, D. J., Mol. Biol. 99: 410–443 (1975). It should be emphasized that after allowing binding of RNA polymerase to ASV DNA to proceed, but prior to the treatment of the complexes with DNAase, a vast excess (aprox. 3000-fold) of denatured calf thymus DNA is routinely added to remove any nonspecific binding of the polymerase to DNA. A more direct test for the stability of binary complexes formed between a specific site on the DNA and polymerase is the resistance of these complexes to heparin (Brown, K. D., Bennet, G. N., Lee, F., Schweingruber, M. E. and Yanofsky, C. J., Mol. Biol. 121: 153–177 (1978)). In experiments which were carried out there was strong evidence for the sensitivity of binary complex formation to heparin. Incubation of the enzyme with heparin before adding DNA substrate completely abolishes binding. As few as two to three molecules of heparin per molecule of RNA polymerase inhibits more than 90% of the binding. However, addition of the inhibitor after allowing formation of the polymerase-DNA complexes is without any significant effect. These results strongly suggest that the binding of RNA polymerase to ASV DNA is tight and specific. The results also show that binding of RNA polymerase to ASV DNA is specific to a nucleotide site which is probably located in the 7 to 9 S DNA.

The yield of the polymerase protected DNA depends on the molar ratio of polymerase to DNA. Approximately a maximum of 5 to 6% of the input DNA of 800-1000 base pairs is observed at an enzyme to DNA molar ratio of 15 to 20. These results are analogous to those observed for several prokaryotic DNAs and E. coli RNA polymerase (Chamberlin, M. J., Ann. Rev. Biochem. 43: 721–775 (1974)). Fractionation of the RNA polymerase-viral DNA complexes on Sephadex G-Lb 100, after extensive nuclease digestion, resolves the complex from digested product. These complexes are obtained in the void volume. No such complexes could be found in the reaction where RNA polymerase was omitted. In order to determine the size of the DNA fragment protected by polymerase, the complexes eluted in the void volume were deproteinized by extraction with phenol and precipitated with ethanol. The fragments were recovered from ethanol by centrifugation and analyzed on a 10% polyacrylamide gel using the buffer described by Pribnow (Pribnow, D. J., Mol. Biol. 99: 419–443 (1975)). The protected fragment comigrated with xylene cyanol dye and calibration by using the R9 (118 base pairs) and R10 (72 base pairs) fragments of φXDNA generated by restriction enzyme Hae III as markers in a parallel slot has indicated that the RNA polymerase-protected fragment in ASV DNA is about 35-40 base pairs long. Under the same conditions of electrophoresis, T7 phage promoter has the same mobility (Pribnow, D. J., Mol. Biol. 99: 419–443 (1975)). Unbound and undigested DNA remained close to the origin even after S1 nuclease treatment, consistent with its size as determined by sucrose gradient. From these results it is concluded that a DNA fragment of about 35 base pairs can be protected from nuclease digestion upon binding to E. coli RNA polymerase and this fragment is located near the 3'-end of the genome.

Evidence that the polymerase binding site is at the 3'-end of ASV DNA: C region

In order to define the RNA polymerase binding region more specifically $^{32}$P-labeled ASV DNA was synthesized and analyzed in velocity gradient. Analysis by S1 nuclease indicated that throughout the gradient, except in the 3 to 4 S region, the DNA is more than 85% double-stranded. To size the DNA more precisely, every three or four fractions were pooled and precipitated with ethanol. The precipitates were collected and analyzed on agarose gels. From the positions of λ and φX174 DNA restriction enzyme fragments, which were run in parallel, somewhat homogenous size classes of DNA ranging from 200 to 4000 base pairs were selected, eluted from the gel and used in the RNA polymerase binding assay. As expected, the DNA fragments that were recovered from the gel were shown to migrate moderately homogeneously in agarose gels.

In order to prove that the selected size classes of DNA are not permuted, the 1500-2000 base pair DNA was digested with restriction enzyme PvuI and Eco RI. The cleavage sites from these enzymes have previously been deduced (Shank, P. R., Hughes, S., Kung, H. J., Majors, J. E., Quintrell, N., Guntaka, R. Vl, Bishop, J. M. and Varmus, H. El, Cell A15: 1383-1395 (1978)). The restriction enzyme PvuI has a single site in the in vitro synthesized DNA of approx. 210 base pairs and Eco RI has one site at 155 base pairs and three other sites to generate three fragments of about 3100, 4200 and 2200 base pairs. PvuI and EcoRI generated 210 and 155 base pairs fragments from the 1500-2000 base pairs in vitro DNA and expected amounts from the size of the 7-9 S DNA were recovered. From the analysis of the fragments with these enzymes one can conclude that at least 80% of the total DNA results from an orderly transcription from the 3'-end. In other words the transcription of viral DNA primarily proceeds from 3' to 5'-end, with respect to virion RNA, as expected. However, the possibility of some (20%) random initiations during reverse transcription is not excluded.

Each size class DNA was reacted with RNA polymerase holoenzyme and the amount of DNA protected from DNAase determined. The results clearly indicate that increasing the size of DNA decreases the percentage of DNA protected by polymerase. For example, when 40 ng/ml of the largest (2500) or smallest (200) base pair DNA is incubated with 0.8 µg/ml E. coli RNA polymerase, 1.8% and 17% are protected from DNAase digestion. Intermediate values are obtained with fragments of different sizes. Treatment of individual fragments with S1 prior to addition of RNA polymerase did not change the results indicating that the polymerase is not binding to the free ends or single strand regions. This and the fact that the 2000-3000 fold excess denatured calf thymus DNA, which was added after allowing binding, did not decrease the yields argues against any nonspecific binding of the polymerase to ASV DNA. These results strongly indicate that a specific RNA polymerase binding site is present in the first 200 nucleotides from the 3'-end. If the binding were random along the genome, then a specific decline in the amount of DNA protected by RNA polymerase would have not been observed. Additional experiments with restriction enzymes confirm these results and define more precisely the site at which the RNA polymerase binds.

In order to map the building site more precisely additional experiments have been carried out with other restriction enzymes. From the sequence data of Schwartz and Gilbert (quoted in Taylor, J. M., in Comprehensive Virology (Frankel, H., Conrat, R. R. and Wager, R. E., eds.) Plenum Press, New York, (1977), it is evident that TaqI has two sites, one immediately adjacent to the short terminal repeat and the other in the strong-stop DNA (101 nucleotides from the 5'-end of the viral genome). One of the TaqI sites overlaps a site for another enzyme, AluI. The sites for these enzymes have been confirmed by isolating a 155 base pair EcoRI fragment followed by digestion with AluI and TaqI. AluI has generated a 35 to 37 base pair fragment and TaqI has yielded three fragments of about 35, 65 and 45 base pairs from the EcoRI fragment (FIG. 1). In order to define the RNA polymerase binding site more exactly the 7 to 9 S DNA was first digested with these enzymes, and then the binding assay was performed. As shown in Table II, the enzymes, AluI, TaqI and EcoRI have considerably reduced the amount of DNA protected by polymerase whereas PvuI and MboI have no effect. The recognition sequence of PvuI contains the sequence for MboI and therefore both generate the same fragment from the 3'-end.

From these data one concludes that the RNA polymerase binding site is indeed located within the first 150 nucleotides of the right hand end of viral DNA or within the first 50 nucleotides (150 minus 101 nucleotide strong stop DNA) of the heteropolymeric region, i.e., in the DNA corresponding to the sequence immediately adjacent the poly(A) region of the RNA genome.

That this binding is not fortuitous is shown by additional experiments with the viral DNA isolated from ASV-infected QT6 cells. If the experiments with the in vitro made viral DNA are valid, the in vivo DNA should have two identical polymerase binding sites since the termini of the in vivo DNA are repeated by about 300 base pairs. Preliminary experiments on the binding of RNA polymerase to specific restriction enzyme fragments of in vivo synthesized ASV DNA validate this prediction. Previously, it has been shown that XhoI digestion of ASV DNA yields four fragments of 2.4, 1.8, 4.7 and 0.7 kilo base pairs from the 3'-end (Hsu, R., Sabran, J. L., Mark, G. E., Guntaka, R. V. and Taylor, J. M., J. Virol. 28: 810-818 (1978); Shank, P. R., Hughes, S., Kung, H. J., Majors, J. E., Quintrell, N., Guntaka, R. V., Bishop, J. M. and Varmus, H. E., Cell 15: 1383-1395 (1978)). It has further been shown that the left end fragment (0.7 kilo base pairs) contains the terminal repeat and if the binding promoter is in the C region, the left end 0.7 kolo base pairs fragment also should have an additional binding site. Therefore, viral DNA isolated from ASV-infected QT6 cells was digested with XhoI, bound to E. coli RNA polymerase and the bound and unbound DNA eluted, concentrated by ethanol precipitation and analyzed on 1% agarose gels. Individual slices were then hybridized to $^{32}$P-labeled virus specific cDNA. The results obtained clearly indicate binding of 2.4 and 0.7 kilo base pair fragments. It should be pointed out that the peak of hybridization to the 2.4 kilo base pairs fragment is broad.

TABLE II

EFFECT OF PRIOR RESTRICTION ENZYME CLEAVAGE
OF ASV DNA ON RNA POLYMERASE BINDING
The 7-9 S viral DNA was purified. The DNA was
treated with each restriction enzyme under the conditions
described by the supplier. The restriction enzyme-cleaved
DNA was deproteinized and reacted with RNA polymerase. The
amount of DNA protected by the polymerase was determined
as in Materials and Methods.

| Treatment | % Protected |
|---|---|
| Control | 6.0 |
| AluI | 2.4 |
| PvuI | 7.0 |
| MboI | 6.5 |
| TagI | 1.3 |
| EcoRI | 2.4 |

This may be due to the presence of transformation defective genomes which lack the 2 kilo base pair Src specific sequences and therefore a new band of about 2.1 kilo base pairs will be at the 3'-end which should bind to RNA polymerase. Also two fragments of about 1.2 and 0.7 kilo base pairs are bound to the polymerase. These are probably due to the heterogeneity of the terminal repeat which ranges from 0.3 to 1 kilo base pairs (Hsu, R., Sabran, J. L., Mark, G. E., Guntaka, R. V. and Taylor, J. M., J. Virol. 28: 810–818 (1978)). Similar experiments with other avian tumor viruses, whose nucleotide sequence at the 3'-end is considerably different e.g., RAV-O, an endogenous virus which is produced from chicken cells in very low quantities (Coffin, J. M., Champion, M. and Chabot, F., J. Virol. 28: 972–991 (1978)), are necessary to establish the significance of $E.$ $coli$ RNA polymerase binding site in ASV DNA.

Discussion

A promoter is operationally defined as a segment of DNA to which the RNA polymerase binds and initiates transcription. The results presented here with avian sarcoma virus DNA and $E.$ $coli$ RNA polymerase indicate such a specific reaction with properties similar to those described for promoters isolated from prokaryote systems. In addition, the RNA polymerase binding site has been localized to within 50 nucleotides. Since the nucleotide sequence of the 3'-end of the ASV genome is available, it is possible to predict whether such a site exists in this region of the viral DNA.

The nucleotide sequence of the DNA for several eukaryotic messenger RNAs and for adenovirus late mRNA are known (Ziff, E. B. and Evans, R. M., Cell 15: 1453–1475 (1978); Konkel, D., Tilghman, S. and Leder, P., Cell 15: 1125–1132 (1978); Gannon, F., O'-Hare, F., Perrin, F., LePennec, J. P., Benoist, C., Cochet, M., Breathnack, R., Royal, A., Garapin, A., Cami, B. and Chambon, R., Nature 278: 428–434 (1979)). From these data several groups have deduced possible promoter sequences by assuming tht the cap site is coincidentally the startpoint of mRNA transcription. Comparison of these promoter sequences with ASV 3'-end sequence indicates the presence of a potential promoter with a fair degree of homology to the $\beta$-globin major promoter. This sequence is located at about 8 to 18 nucleotides upstream from the short terminal repeat (startpoint for RNA transcription). Further, when all these sequences are aligned so as to emphasize maximum sequence homologies, clearly there is an 8 base pair A.T-rich region of homology approx. 28 base pairs upstream from the initiating nucleotide of the ASV 35s RNA.

Although the $E.$ $coli$ RNA polymerase protected DNA fragment has not been sequenced, it has been shown that prior digestion of the DNA with AluI and TaqI greatly reduces $E.$ $coli$ RNA polymerase binding. Since the recognition sites for both enzymes are within the putative ASV promoter sequence, this suggests that the RNA polymerase recognizes this sequence specifically. In view of the fact that a promoter, isolated from SV40 DNA by virtue of its binding to $E.$ $coli$ RNA polymerase (Dhar, R., Weissman, S. M., Zain, F. S., Pan, J. and Lewis, Nucleic Acid Res. 1: 595–614 (1974), has been shown not to be utilized by eukaryotic RNA polymerase II, one would be cautious in defining the RNA polymerase site on ASV genome, a promoter. Whether eukaryotic RNA polymerase II binds to the same site remains to be determined.

SECOND SERIES OF EXPERIMENTS

In the First Series of Experiments specific binding of $E.$ $coli$ RNa polymerase holoenzyme to a site located in the C region of avian tumor virus DNA was demonstrated. Precise location of this site was achieved by first digesting the DNA with various restriction endonucleases followed by RNA polymerase binding. These results indicated that the binding site is in the vicinity of the short terminal redundant sequence somewhere between the EcoRI and AluI/TaqI sites (Guntaka, R. V., Rao, P. Y., Katz, R. A. and Mitsialis, S. A., Biochim. et Biophys. Acta, (in press)). In order to test whether the same binding site is utilized by RNA polymerase in transcribing viral RNA, two Hind III fragments of avian tumor virus DNA were cloned in $E.$ $coli$ plasmid pBR322.

The RNA genome of avian tumor viruses is shown in FIG. 2A. The stock of Prague C strain of avian sarcoma virus which was used in these experiments contains both nondefective and transformation-defective infectious virus particles. The latter lacks a sequence called src (Wang, L. H., Ann. Rev. Microbiol., 32: 61–92 (1978)). All of these viruses, however, contain the C region as well as the short terminal repeat of 21 nucleotides (Bishop, J. M., Ann. Rev. Biochem., 47: 35–88 (1978); Wang, L. H., Ann. Rev. Microbiol., 32: 61–92, (1978)). During the process of conversion of RNA into duplex DNA, a portion of the C region is duplicated to give rise to two large terminal repeats of about 300 nucleotides (Hsu, T. W., Sabran, J. L., Mark, G. E., Guntaka, R. V. and Taylor, J. M., J. Virol., 28: 810 $\propto$ 818 (1978); Shank, P. R., Hughes, S. H., Kung, H. J., Majors, J. E., Quintrell, N., Guntaka, R. V., Bishop, J. M. and Varmus, H. E., Cell, 15: 1383–1395 (1978)). These large repeats are present in some of the linear (FIG. 2B) as well as circular DNA molecules (FIG. 1D). All possible structures are shown in FIG. 1. The cleavage maps for some restriction enzymes are also shown in FIG. 1. The DNA fragments cloned in the present work were derived from a transformation-defective circular DNA which had only one copy of the C region and thus had only one LTR. (FIGS. 1C and 1E). Since the cloned DNA does not contain src-specific sequences, the virus has been designated avian tumor virus, (ATV), and the fragments cloned in pBR322, pATV.

Figure 2:
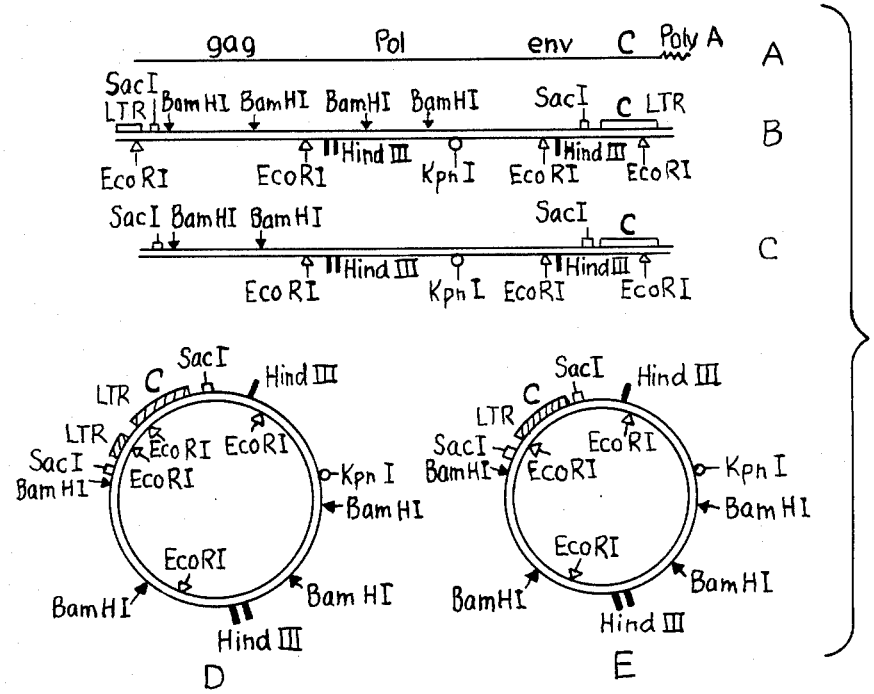
FIG. 2. Schematic representation of the avian tumor virus RNA and DNA genome. A is the 35S RNA subunit. B and D are linear and circular DNA containing two large terminal repeats. C and E are linear and circular DNA containing only one large terminal repeat. LTR stands for large terminal repeat. C refers to the common or constant region. Cleavage sites for pertinent restriction endonucleases are indicated.

Hind III cleaves the circular DNA at three sites to yield three fragments of 4.2, 3.2 and 0.15 kb. FIG. 2) The 4.2 kb contains a small portion of the env gene, a complete copy of the C region, a complete gag gene and a portion of the pol gene. (FIG. 2) The 3.2 kb fragment contains the remainder of the env gene and some sequences corresponding to the pol gene. In order to clone viral DNA fragments, circular ATV DNA was digested with Hind III and ligated to plasmid pBR322 DNA at the corresponding Hind III site as described in the Methods and Materials. Several transformants were selected and analyzed for viral DNA inserts by colony hybridization using virus-specific $^{32}$P-labeled cDNA reagent. DNA was isolated from positive clones and analyzed by gel electrophoresis for the size and orientation of the viral DNA inserts. One clone, pATV 2.11, contained the 3.2 kb insert as evidenced by the appearance of two fragments of 4.3 and 3.2 kb upon Hind III digestion. To detect the fragment containing viral sequences, the DNA from the gel was transferred to cellulose nitrate paper andd hybridized with radioactively labeled virus-specific cDNA. Only the 3.2 kb fragment showed hybridization. The orientation of the inserted fragment was then deduced by using a variety of restriction endonucleases whose cleavage sites on the viral genome are known.

Characterization of Viral DNA inserts

EcoRI yielded a major fragment of 7.3 kb and a small fragment of 0.2 kb. Three fragments of 5.58, 1.11 and 0.89 kb were obtained with BamHI. Since BamHI cleave pBR322 DNA at a site about 0.35 kb towards the right of hind III site, the order for the viral DNA insert in clone pATV 2.11 must be as depicted in FIG. 3A. Similar gel electrophoresis analysis of Hind III, EcoRI, and BamHI followed by hybridization revealed the opposite orientation for the 3.2 kb fragment in clone pATV 2.13. Hind III gave fragments of 4.3 and 3.2 kb, EcoRI generated two fragments of 4.35 and 3.14 kb and BamHI, as expected, cleaved at three sites to give rise to 4.80, 1.8 and 0.89 kb fragments. These data were further confirmed by simultaneous digestion with two restriction enzymes.

Similar analysis with appropriate restriction enzymes indicated an orientation (FIG. 3C) for the 4.2 kb insert in clone pATV.6. Hind III, as expected, gave only one band of about 4.3 kb because of the same size of the inserted fragments as pBR322. EcoRI generated three fragments of 4.7, 2.43, and 1.38 kb fragments and BamHI yielded three fragments of 6.24, 1.23 and 1.0 kb whereas simultaneous digestion with Hind III and BamHI gave four fragments of 4.04, 2.18, 1.23 and 0.65 kb. SacI gave rise to two fragments of 4.35, 2.59, 1.03 and 0.48 kb. Given the cleavage sites for these enzymes on ATV as well as pBR322 DNAs, the order shown in FIG. 3C could be deduced for the 4.2 kb insert. The opposite orientation was derived for clone pATV-5RI from a similar restriction enzyme analysis of the DNA. For example, Hind III, as expected, gave a pattern identical to pATV-6. EcoRI, in contrast to pATV-6, yielded a larger fragment of 5.4 and a smaller fragment of about 0.6 kb in addition to the middle 2.43 kb fragment.

Figure 4:
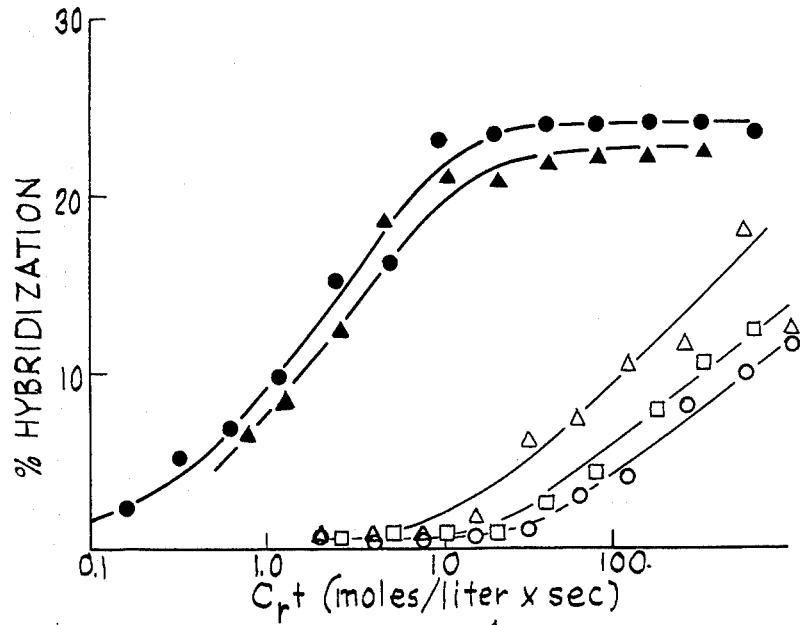
FIG. 4. Evidence for transcription of viral RNA. RNA was extracted from each plasmid recombinant by the cesium chloride method and hybridized to $^{32}$P-labeled virus-specific cDNA as described in Methods and Materials. The amount of hybridization was determined by treating with S1 nuclease. Approximately 6,000 to 10,000 cpm (sp. act. $3\times10^5$ cpm/ng) of cDNA was used in each reaction. (O)pATV-6; (Δ)pATV 2.13; (O) pATV 2.11 (□)pATV 2.13. pATV-2.14 has the same orientation as pATV 2.13. (Δ)pATV-6.1
Figure 5:
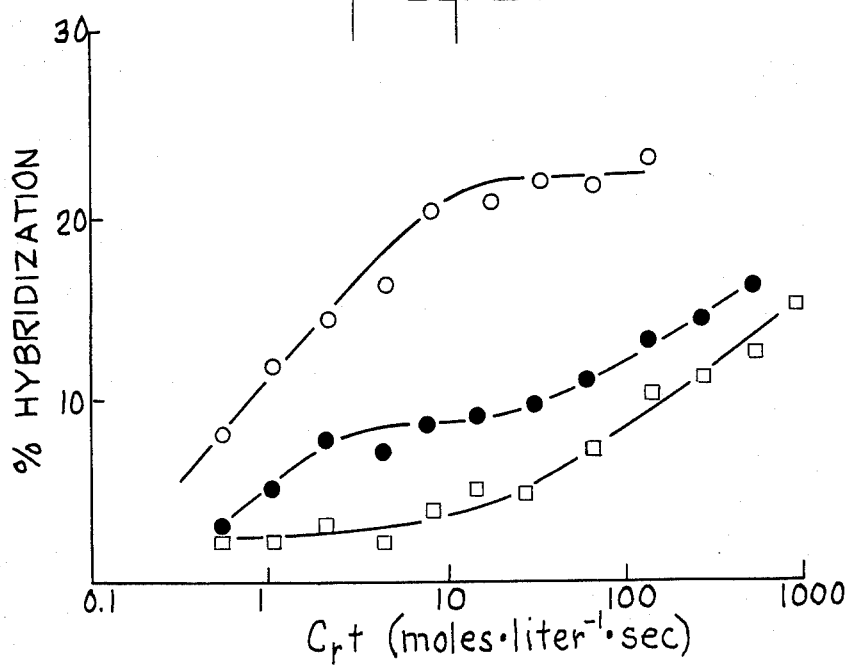
FIG. 5. Evidence for a promoter site in pATV-6. RNA was isolated from pATV-6, pATV-6 SAC.RI and pATV-6. ΔS recombinants and hybridized at various dilutions to a constant amount (6,000 to 10,000 cmp) of $^{32}$P-CDNA. The conditions and extent of hybridization were as described above. (O)pATV-6; (O)pATV-6. SACR1; (□)pATV-6.ΔS.

BamHI gave three fragments of 4.80, 2.5 and 1.23 kb. SacI gave two bands of 7.4 and 1.03 kb as in pATV-6. As shown in the First Series of Experiments, *E. coli* RNA polymerase binds to a site which is located in the C region. If this binding reflects a promoter activity for this site one would anticipate transcription of high levels of viral RNA in *E. coli*. The four clones obtained above are ideal for such studies. Therefore, in order to detect any viral RNA synthesis, total cellular RNA was isolated from all four clones and assayed for virus-specific RNA by hybridizing to $^{32}$P-labeled cDNA and the extent of hybridization was monitored by S1 nuclease (Guntaka, R. V. and Weiner, A. J., Nature, 253: 274–276 (1978)). The results presented in FIG. 4 provide evidence for the synthesis of large quantities of viral RNA in pATV-6. A $C_rt$ ½ of about 2 to 3 was obtained with RNA from pATV-6 irrespective of the orientation. (FIG. 4) This indicates that approximately 0.5 to 1.0% of the total cellular RNA was virus-specific as computed from the $C_rt$ ½ $=2\times10^{-2}$ obtained with purified viral 70S RNA.

In different experiments, about 24 to 30% of the input $^{32}$P-cDNA was rendered resistant to S1 nuclease. This is not unexpected because the cDNA reagent used for hybridization represented the entire viral genome which is 10,000 nucleotides long whereas the size of RNA expected from the 4.2 kb insert is less than 3 kb or 30% of the $^{32}$P-labeled cDNA assuming complete representation of 10 kb genome. Thus, the extent of hybridization observed is in good agreement with the expected level. The 30–32% value was obtained with $^{32}$P-cDNA prepared from 70S RNA which was isolated from a transformation-defective virus stock.

In contrast to pATV-6, very little ($C_rt$ ½ = <100–600) RNA was transcribed in pATV 2.11. (FIG. 4) The orientation of the 3.2 kb insert did not make any difference in the level of RNA transcription as indicated by similar $C_rt$ ½ for pATV 2.13. These results strongly suggest that viral RNA transcription in pATV-6 takes place using a viral promoter. The fact that reserving the orientation of the 4.2 kb insert in pATV-6RI neither altered the kinetics nor the extent of hybridization provides strong evidence for a promoter in pATV-6.

Figure 3:
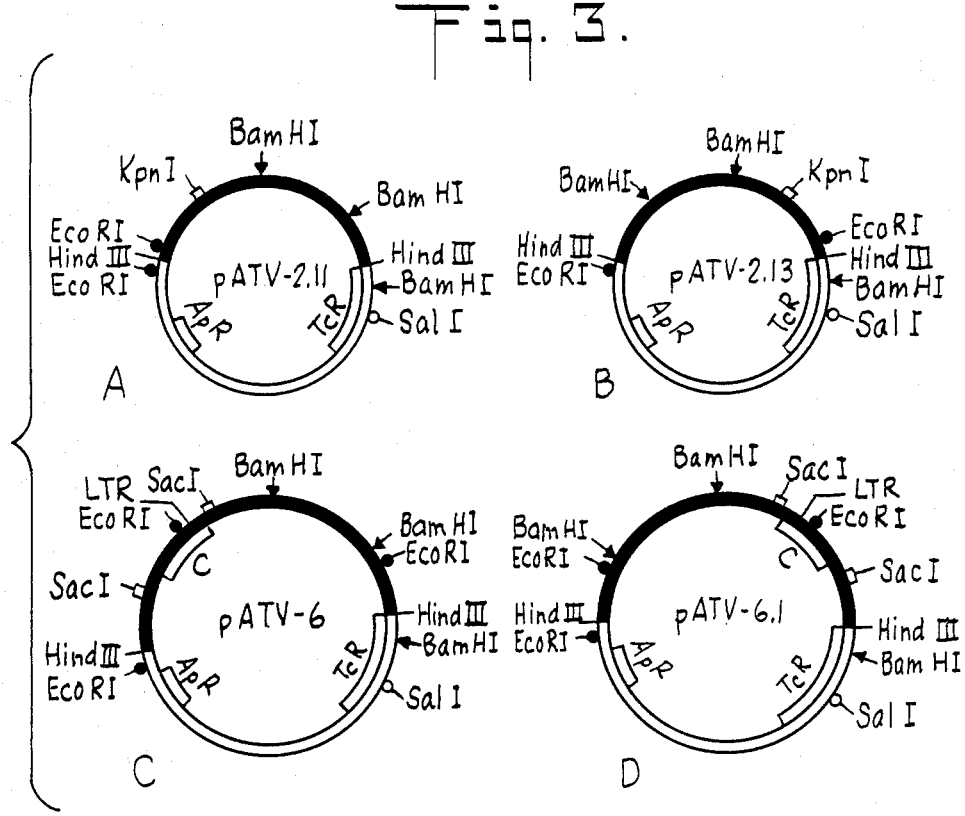
FIG. 3. Orientation of the viral DNA insert in different recombinant clones. The arrangement of all the inserts was deduced from gel electrophoresis data as well as from other restriction endonuclease analysis. Dark lines refer to the inserts and white lines indicate pBR322 genome. LTR and C are as described in the legend to FIG. 2.

Proof that viral RNA transcription begins in or around the C region was obtained by subcloning experiments. As depicted in FIG. 3, SacI cleaves the 4.2 kb viral DNA insert at two places which are on either side of the C region or LTR to yield a fragment of 1 kb. This enzyme does not cleave the pBR322 or the 3.2 kb insert. If the promoter site is located in the C region, removal of the 1.0 kb fragment should eliminate the promoter activity. To test this hypothesis, pATV-6 DNA was digested wtih SacI, the resulting 7.5 (L) and 1.03 (S) kb fragments were separated on velocity sucrose gradients and the L fragment alone or L+s fragments were ligated with T4 ligase. The DNA was then used to transform *E. coli* HB101. Transformants were screened for $Ap^R$, and the DNAs were isolated from the desired clones and analyzed for the deletions of S fragment. The results obtained indicated the required arrangement of the insert in the three clones. For example, when the pATV-6 DNA was digested with EcoRI three fragments of 4.7, 2.43 and 1.38 kb were obtained. pATV 6.SAC.ΔS on the other hand lacked the 1.0 kb fragment. As a result, the EcoRI site in the LTR was missing and therefore only two fragments of 4.7 and 2.71 kb were evident. pATV.6SAC.RI, upon digestion with EcoRI yielded three fragments as in pATV-6, but instead of the 2.43 and 1.38 kb fragments, two new fragments of 2.68 and 1.10 kb SacI fragment was reversed in this clone. In such a situation the EcoRI site in the LTR would be much closer to the EcoRI site in pBR322 and thus a larger site (1.68 kb) fragment. A corresponding decrease in the 1.38 kb fragment of pATV.6 was evident in pATV.6.SAC.RI.

The cellular RNA isolated from these three clones was tested for virus-specific sequences as described for FIG. 4. As observed above, the $C_rt$ ½ for pATV.6 was between 2 and 3 and the amount of hybridization reached a plateau at about 22%. In contrast, very little if any virus-specific RNA was transcribed in pATV-6.SACΔS. This result indicates that a site located in the 1.0 kb SacI fragment is crucial for viral RNA transcription, further supporting earlier observations. In pATV-6.SAC.RI a low $C_rt$ ½ was observed analogous to pATV-6, but the extent of hybridization indicated that the amount of virus-specific RNA at the plateau was only about 6 to 8%. This was not surprising because, in the leftward orientation, virus-specific RNA equivalent to only about 0.7 out of 9.8 kb genome could be transcribed. These results provide convincing evidence for the occurrence of a promoter sequence in or around the C region and that *E. coli* RNA polymerase utilizes this very efficiently in transcribing viral RNA sequences.

Figure 6:
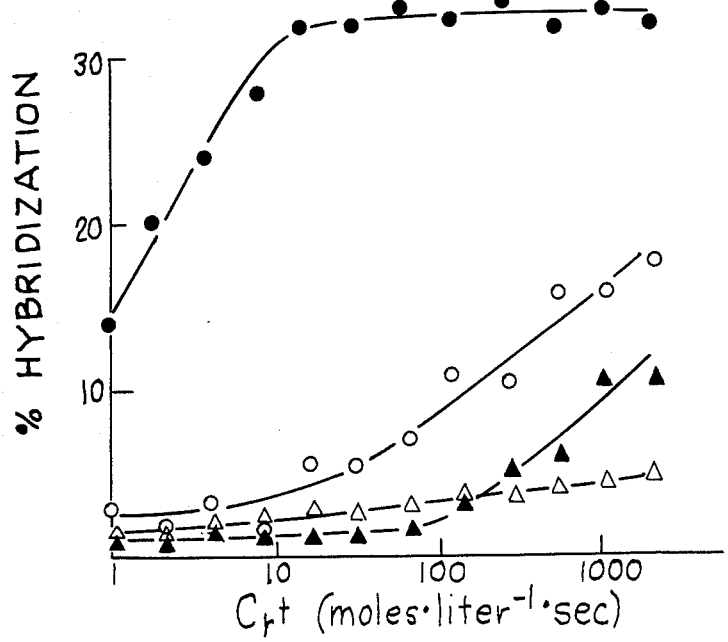
FIG. 6. Evidence for the transcription of viral RNA of genome polarity. RNA was purified from pATV-6 and pATV 2.11 and hybridized to $^{32}$P-labeled cDNA or $^{32}$P-labeled 70S RNA and the extent of annealing was monitored by S1 nuclease in case of cDNA or pancreatic ribonuclease in case of 70S RNA. Specific activity of $^{32}$P-70S RNA was about 1.5 to $2\times10^4$ cpm/ng and 800 cpm were used in each reaction point. pATV-6 RNA was hybridized to $^{32}$P-labled cDNA (O) or $^{32}$P-labeled 70S RNA (Δ); pATV 2.11 RNA was hybridized to cDNA (O) or 70S RNA (Δ); pATV 2.11 RNA was hybridized to cDNA (O) or 70S RNA (▲). In this experiment, 70S RNA used to prepare $^{32}$P-labeled cDNA was derived from transformation-defective virus. That is why about 32% of the cDNA was rendered resistant to S1 nuclease as opposed to 22–24% in other experiments.

The above results demonstrate synthesis of viral RNA of messenger polarity (virion RNA) since it was detected by using $^{32}$P-labeled cDNA. In order to test whether virus specific negative strand RNA was transcribed, cellular RNAs isolated from pATV-6 and pATV-2.11 were hybridized to $^{32}$P-labeled viral RNA which was purified from isolated virus particles. The data presented in FIG. 6 clearly show that while in pATV 2-11 both stands were transcribed at a very low level as indicated above, in pATV-6, the plus strand (messenger a virion or sense RNA strand) synthesis was at least 80 to 100-fold more efficient than the negative strand. From these data, one can conclude that *E. coli* RNA polymerase recognizes and transcribes viral RNA of correct polarity.

Finally, it should be mentioned that pATV-6 rendered the transformants resistant to 5 μg/ml tetracycline (Tc). Support for this came by direct growth measurements of different clones in L broth containing various concentrations of Tc. Since Hind III cleavage of plasmid DNA interrupts the promoter for Tc, the results with pATV-6 imply that the viral promoter can substitute for the Tc promoter. This may be achieved by a read-through of viral RNA into the Tc gene. Further analysis is required to substantiate this observation.

Discussion

The construction of plasmids carrying avian tumor virus DNA fragments has been described. It has been shown that at least one viral fragment contains a promoter sequence recognized by *E. coli* polymerase. In order to clone the viral DNA fragments, avian tumor virus covalently closed circular DNA was digested with Hind III and the fragments were inserted at the Hind III site in pBR322. Recombinants were selected and the orientation of the inserts deduced by analyzing the DNA, digested with various restriction enzymes, on agarose gels. Two fragments of 4.2 and 3.2 kb were thus inserted in the two orientations possible for each insert.

The major interest in obtaining these recombinants is to test whether ATV genome carries a promoter site. This interest stems from the fact that *E. coli* RNA polymerase holoenzyme binds strongly to a site located immediately adjacent to the 3'-end of this genome, which is usually referred to as large terminal repeat (LTR), located within the C region (FIG. 2). From studies on the efficiency of transcription. (Guntaka, R. V., Rao, P. Y., Katz, R. A. and Mitsialis, S. A., Biochim. et Biophys. Acta, (1980) in press; Taylor, J. M., Mason, W. S., Hsu, T. W., Sabran, J. L., Yeater, C. Mark, G. E., Kaji, A., Guntaka, R. V. and Lai, M. M. C., Cold Spring Harbor Symp. Quant. Biol., 43: 865–867 (1979)) and others (Tsichlis, P. N. and Coffin, J. M., J. Virol. 33:238-249 (1980)), the presence of a potential promoter had been postulated. This promoter must be unique with respect to its affinity for RNA polymerase II so as to allow transcription of large quantities of viral RNA (5–10% of total polyA+ RNA) in permissive cells.

The results presented here, though they do not identify the precise sequence at which transcription begins, nevertheless shows that this sequence lies within the 1.0 kb SacI fragment of pATV-6 as evidenced by the decreased levels of viral RNA in the subclones of pATV-6 in which this fragment was deleted or reversed in orientation.

Although RNA of genomic polarity is the predominant product, transcription of small amounts of negative strand RNA was not excluded. More experiments using specific restriction enzyme fragments of pATV-6 and pATV-2, which are labeled to high specific activity by nick translation, are necessary to increase the sensitivity of detection of negative strands of viral RNA and to locate the exact site in the 1.0 kb SacI fragment where transcription initiates.

Identification and isolation of this promoter sequence is of utmost importance in recombinant DNA research. If this promoter can transcribe other DNA fragments as efficiently as tumor virus DNA fragments, then these findings have potential applications in transcribing other Eukaryotic genes in *E. coli*. Such studies with globin, adenovirus hexon, thymidine kinase and immunoglobulin genes are in progress. Experiments to determine the translational products of viral genes are also in progress.

MATERIALS AND METHODS

Viruses. Avian sarcoma virus Prague C (subgroup C) or Prague B (subgroup B) were grown in chick embryo fibroblasts. Chick embryos were obtained from Spafas Poultry Farm (Norwich, CT). Virus purification was achieved by standard procedures which involve pelleting the virus from clarified medium followed by banding in sucrose gradients. Prague C was sometimes obtained from the University Laboratories though the Office of Logistics and Resources of the National Cancer Instiututes. This virus, which was concentrated approx. 130-fold prior to shipping, was purified as above.

Preparation of viral DNA. About 2–4 mg virus was incubated at 37° C. for 18–20 h in a reaction volume of 1 ml containing high deoxynucleoside triphosphates (P-L Biochemicals, Milwaukee, Wis.) essentially as described by Rothenberg and Baltimore (Rothenberg, E. and Baltimore, D. J. Virol. 17: 168–174 (1976)) except that actinomycin D was omitted from the reaction and NP-40 was used at 0.02%. Varying the $Mg^{2+}$ concentration from 4 to 8 mM did not make much difference with respect to the yields or size of the product. $^3$H- or $^{32}$P-labeled deoxyribonucleoside triphosphate was present usually at 0.1 mM. The product thus synthesized had a specific activity ranging from 2 to $4 \times 10^6$ cpm/μg DNA. At the end of the reaction, EDTA and SDS were added to a final concentration of 20 mM and 0.2% and the lysate was treated for 1 h with 200 μg/ml proteinase K. Following phenol extraction the nucleic acids were precipitated with ethanol at $-20°$ C. for 20 to 24 h. The precipitates were collected by centrifugation at $12000 \times g$, washed with 70% ethanol, dried and then resuspended in 10 mM EDTA. The solution was treated successively, with 100 μg/ml pancreatic ribonuclease A (Worthington) for 1 h. at 37° C. and 100 μg/ml proteinase K for 30 min. at 37° C. Phenol extraction and ethanol precipitation were as above.

Sedimentation of viral DNA. $^3$H- or $^{32}$P-labeled viral DNA prepared as above was layered onto a gradient of 5–20% sucrose dissolved in 100 mM NaCl, 20 mM Tris-HCl, pH 8.1, 3 mM EDTA and centrifuged in a SW41 rotor for 16 h at 25000 rev./min. and 20° C. Fractions were collected from the bottom of the gradient. Aliquots from individual fractions were precipitated directly with trichloroacetic acid or first treated with 300 units single-strand, specific S1 nuclease (Miles Laboratories, Elkhart) in 300 mM NaCl, 30 mM sodium acetate bubber, pH 4.5, 3 mM $ZnCl_2$ and 10 μg/ml denatured calf-thymus DNA for 2 h. at 50° C. followed by precipitation with trichloroacetic acid. The precipitates were collected on glass fiber filters (GF/C), dried and counted in econofluor (New England Nuclear, Boston, Mass.)

Gel electrophoresis. Avian sarcoma virus DNA of discrete size classes were selected from the sucrose gradients, pooled and precipitated by 2 vols of ethanol at −20° C. The precipitates were collected by centrifugation, resuspended in the loading buffer (10 mM Tris-HCl, 0.1% Bromophenol blue and 10% sucrose) and analyzed on 1% agarose vertical slab gels (20×14 cm) in a Tris-borate buffer. The gels were run at 35 V for 11 h. Hind III digested bacteriophage λDNA (Bethesda Research Laboratories, Rockville, Md.) was run in a parallel slot as a marker. After electrophoresis, the gels were stained with 1 µg/ml ethidium bromide and the bands were located under ultraviolet light source. The DNA of the appropriate size was eluted from agar slices essentially as described in Maxam, A. and Gilbert, W., Proc. Natl. Acad. Sci. U.S.A., 74: 560–564 (1977)). The size of the eluted size classes was confirmed by re-analyzing on the same 1% agarose gels.

Assay for E. coli RNA polymerase binding to ASV DNA. This assay, which measures the amount of DNA that was protected from deoxyribonuclease as a result of RNA polymerase binding, was based on the conditions described in Heyden, B., Nusslein, C. and Schaller, H., Nature New Biol. 96:9–12 (1972). The standard binding reaction was carried out in a 50 to 100 µl volume containing 0.3M KCl, 50 mM Tris-HCl, pH 7.5, 10 mM $MgCl_2$, 200 µg/ml bovine serum albumin, 0.3 mM ATP, 0.3 mM GTP, 5% glycerol, 10 to 20 ng $^3H$- or $^{32}P$-labeled viral DNA (7 to 9 S) and 0.2 to 0.4 µg E. coli polymerase holoenzyme. The enzyme was purified by published procedures (Burgess, R. R., and Jendrisak, J. J., Biochemistry, 14: 4634–4433 (1975)). After incubating for 5 to 10 min. at 37° C., 200 µg/ml denatured calf thymus DNA was added and the tubes were incubated for an additional 5 min. Then the reaction mixture was diluted with Tris-HCl buffer containing the same concentration of $MgCl_2$, bovine serum albumin, ATP, GTP and glycerol to give a final KCl concentration of 0.1M, followed by digestion with 200 µg/ml pancreatic deoxyribonuclease I for 15 min. at 37° C. The samples were filtered through 2.4 cm millipore filters, washed with 50 mm Tris-HCl, 0.3M KCl, 200 µg/ml bovine serum albumin and 5% glycerol. The filters were dried under infrared lamp and the radioactivity was determined in a Searle scintillation counter using econofluor as the scintillant.

Isolation of RNA polymerase protected ASV DNA. About 300 to 400 ng viral DNA (2 to 4×$10^6$ cpm/µg) was incubated with RNA polymerase at an enzyme to DNA ratio of 20 under standard reaction conditions. Following DNAase treatment, the enzyme-DNA complexes were isolated on Sephadex G-100 column (0.7×16 cm) essentially as described in Heyden, B., Nusslein, C. and Schaller, H., Nature New Biol.,96:9–12 (1972). The complexes eluted in the void volume were extracted with phenol. The resulting nucleic acids were precipitated by ethanol at 20° C. The DNA was collected by centrifugation and its size was determined on polyacrylamide gels using the buffer system of Pribnow (Pribnow, D. M., Mol. Biol. 99:419–443 (1975)).

Purification of Avian tumor virus DNA. For the cloning experiments, Avian tumor virus (ATV) specific supercoiled viral DNA was separated from Prague-C ATV-infected quail tumor cell line essentially as described in Guntaka, R. V., Anal. Biochem. 90:256–261 (1978). Briefly, nuclei were prepared from 24 hour-infected cells, lysed in water, chromatin precipitated by 0.25M NaCl and the precipitate collected by low speed centrifugation. The clear supernatant was deproteinized by phenol extraction and the nucleic acids were precipitated by ethanol at −20° C. The precipitates were collected by centrifugation and supercoiled DNA was isolated by CsCl-propidium diiodide gradient centrifugation followed by BND-cellulose chromatography. (Guntaka, R. V., Richards, O. C., Shank, P. R., Kung, H. J., Davidson, N., Fritsch, E., Bishop, J. M. and Varmus, H. E., J. Mol. Biol., 106:337–357 (1976)). Throughout the purification steps viral DNA was monitored by nucleic acid hybridization using radiolabeled viral cDNA. (Guntaka, R. V., Richards, O. C., Shank, P. R., Kung, H. J., Davidson, N., Fritsch, E., Bishop, J. M. and Varmus, H. E., J. Mol. Biol., 106:337–357 (1976)).

Preparation of virus specific radioactive reagents. For the cloning experiments, Avian tumor virus-specific DNA (cDNA) complementary to virion RNA was prepared by the method of Taylor, J. M., Illmensee, R. and Summers, J., Biochim. Biophys. Acta, 442:324–330 (1976). The reaction contained 1 to 2 µg Prague C 70S RNA, α-$^{32}$p-dCTP (300–500 Ci/mmole, New England Nuclear, Boston, Mass.) at a concentration of 10 µM and the three other deoxyribonucleoside triphosphates (P-L Biochemicals, Milwaukee, Wis.) at 500 to 1000 µM, 5 mM dithiothreitol, 6 mM $MgCl_2$, 50 mM Tris-HCl, pH 8.0 and 8 to 10 units (2000 units/mg) avian myeloblastosis virus reverse transcriptase (obtained through the Office of Logistics and resources, National Cancer Institutes), 200 µg calf-thymus DNA primer and 50 µg/ml actinomycin D in a 100 µl volume at 37° C. for 15 to 16 hours. The product was isolated and treated with 0.3M NaOH to remove template RNA and used as a reagent. The cDNA prepared in this way is highly representative of all the sequences in RNA. This cDNA was used to assay for viral RNA.

$^{32}P$-labeled 70S RNA was prepared from the virus as described by Cordell, B., Stavnezer, E., Friedrich, R., Bishop, J. M. and Goodman, H. M., J. Virol., 19:548–558 (1976). Chick embryo fibroblasts infected by Prague C avian sarcoma virus were labeled with 1 mCi/ml carrier-free $^{32}PO_4$ for 24 hours in phosphate-free growth medium and the virus released into the medium was collected, cell debris removed and the virus pelleted at 35,000 rpm in a SW41 rotor at 4° C. for 1 hour. RNA was extracted from the sedimented viral particles. RNA labeled by this method gave specific activities ranging from 10 to 20×$10^6$ cpm/µg.

Ligation of viral DNA fragments to pBR322 DNA. Five ng avian tumor virus supercoiled DNA was mixed with 200 ng pBR322 circular DNA (BRL, Bethesda, Md.) and digested with 2 to 4 units restriction endonuclease Hind III (BRL, Bethesda, Md.) under the conditions specified by the supplier. Following digestion, the nucleic acids were deproteinized and precipitated by ethanol. The precipitates were collected by centrifugation and resuspended directly in 10–20 µl ligase buffer (20 mM Tris HCl, pH 7.6, 6.6 mM $MgCl_2$, 10 mM Dithiothreitol and 0.1 mM ATP). Ligation was carried out at 15° C. for 16–20 hours with 0.5 to 1.0 unit of $T_4$ DNA ligase (Bolivar, F., Rodriguez, R. L., Betlach, M. C. and Boyer, H. W., Gene, 2:75–93 (1977)). The extent of the reaction was monitored by analyzing samples on agarose gel followed by blotting according to the procedure of Southern, E. M., J. Mol. Biol. 98:503–517 (1975)

and nucleic acid hybridization to detect viral DNA using $^{32}$P-labled cDNA.

Transformation of *E. coli* HB101. Transformation of *E. coli* strain HB101 was carried out essentially as described by Kushner, S. R., in *Genetic Engineering*, H. W. Boyer and S. Nicosia, eds. Elsiever/North Holland Biomedical press, Amsterdam, The Netherlands, pp. 17-23 (1978). Transformants were scored on LB agar plates containing 250 μg/ml ampicillin (Ap.). (Bolivar, F., Rodriguez, R. L., Betlach, M. C. and Boyer, H. W., Gene, 2:75-93 (1977)). Because Hind III cleaves within the promotor for the tetracycline resistance (Tc$^R$) gene, insertion of any foreign DNA into this site should result in Tc$^S$ (Bolivar, F., Rodriguez, R. L., Betlach, M. C. and Boyer, H. W., Gene, 2:75-93 (1977)). However, as discussed below, this was not the case with some transformants. Therefore, both Tc$^S$ and Tc$^R$ colonies were tested for viral DNA inserts by colony hybridization (Grunstein, M. and Hogness, D. S., Proc. Natl. Acad. Sci. USA, 72:3961-3865 (1975)) using $^{32}$P-labled virus-specific cDNA.

Preparation of Recombinant DNAs. Colonies of transformants containing viral DNA fragments were grown in L broth. (Bolivar, F., Rodriguez, R. L., Betlach, M. C. and Boyer, H. W., Gene, 2:75-93 (1977)) and plasmid DNA, amplified with 100 μg/ml chloroamphenicol, was prepared by the SDS-NaCl method. (Clewell, D. B., J. Bacteriol., 110:667-676 (1972)). The DNA was further purified on CsCl-Propidium diodide gradients. (Guntaka, R. V., Richards, O. C., Shank, P. R., Kung, H. J., Davidson, N., Fritsch, E., Bishop, J. M. and Varmus, H. E., J. Mol. Biol., 106:337-357 (1976)).

Gel Electrophoresis. For the cloning experiments the size and orientation of the inserted viral DNA fragment was determined on 1% (Seakem) slab gels (20×15×0.3 cm) using the Tris-EDTA borate buffer system of Bolivar, F., Rodriguez, R. L., Betlach, M. C. and Boyer, H. W., Gene, 2:75-93 (1977) after digesting the DNA with appropriate restriction enzymes (Hsu, T. W., Sabran, J. L., Mark, G. E., Guntaka, R. V. and Taylor, J. M., J. Virol. 28:810-818 (1978); Shank, P. R., Huges, S. H., Kung, H. J., Majors, J. E., Quintrell, N., Guntaka, R. V., Bishop, J. M. and Varmus, H. E., Cell, 15:1383-1395 (1978)).

Nucleic Acid Hybridizations. The DNA in the gel was denatured by 1M NaOH, neutralized with 1M HCl and 1M Tris-HCl, pH 7.5 and transferred to cellulose nitrate paper (Schleicher and Schuell) by the methods of Sourthern, E. M., J. Mol. Biol., 98:503-517 (1975) as modified by Wallwijk, C. and Flavell, R. A., Nucl. Acids Res, 5:3231-3232 (1978). Virus-specific sequences were detected by hybridization to $^{32}$P-labeled cDNA. Details of these procedures are published. (Hsu, T. W., Sabran, J. L., Mark, G. E., GUntaka, R. V. and Taylor, J. M., J. Virol. 28:810-818 (1978); Guntaka, R. V., Rao, P. Y., Mitsialis, S. A. and Katz, R. A., J. Virol., (1980), in press.

The clones of *E. coli* containing the viral DNA fragments were grown in L broth to logarithmic phase and RNA was extracted by the CsCl method (Glison, V., Crkenzakov, R. and Cyris, C., Biochemistry, 13: 2633-2637 (1974); Guntaka, R. V. and Weiner, A. J., Nature, 253: 274-276 (1978)). Virus-specific RNA, synthesized in *E. coli*, was detected by liquid hybridization using $^{32}$P-labeled cDNA or 70S RNA. Hybridizations were carried out at 68° C. in 40 μl of 0.6M NaCl, 10 mM Tris-HCl, pH 8.1, 3 mM EDTA and 2000 to 10,000 cpm cDNA (Sp. act. 200-300×10$^3$ cpm/ng) or 800-1000 cpm 70S RNA (Sp. act. 10-20×10$^3$ cpm/ng). Increased concentrations of bacterial RNA were used to obtain the desired C$_r$t (concentration of RNA in moles/liter×time in seconds). Following 15-16 hour hybridization the extent of hybridization was monitored by digesting with single-strand specific S1 nuclease (Guntaka, R. V. and Weiner, A. J., Nature, 253: 274-276 (1978)) or by digestion with pancreatic ribonuclease (50 μg/ml) in 2×SSC (0.15M NaCl, 0.015M sodium citrate) at 37° C. for 1 hour. The nuclease-resistant fraction was precipitated with TCA and the radioactivity was determined by counting in a scintillation spectrometer using Econoflour. (New England Nuclear, Boston, Mass.).

The preceding description has concerned the 35 base pair region of viral DNA which binds RNA polymerase and is a promoter of RNA synthesis. As is well known, there are additional nucleotides necessary for actual transcription of DNA into RNA. In avian tumor viral DNA, there is such a nucleotide region approximately 30-50 nucleotides upstream from the promotor site which is recognized by RNA polymerase before initiating transcription. As used herein, it is to be understood that molecules which include the promoter and genes associated with production of desired products include the additional nucleotides necessary to render the molecules capable of being transcribed into RNA.

What is claimed is:

1. A molecule of double-stranded DNA having a length of about 35 base pairs useful as a promoter of gene expression in *E. coli*, which molecule has the base pair sequence which binds *E. coli* RNA polymerase, said sequence being found in the first 150 base pairs at the 3'-end of Avian sarcoma viral DNA.

2. A molecule of double-stranded DNA which includes the promoter molecule of claim 1 and at least one double-stranded DNA gene, said gene being associated with production of a desired chemical product.

3. A molecule in accordance with claim 2 wherein the gene does not naturally occur in the same molecule as the promotor molecule.

4. A molecule in accordance with claim 2 wherein the desired chemical product is a polypeptide or a compound containing a polypeptide portion and the gene codes for said polypeptide or polypeptide portion.

5. A molecule in accordance with claim 4 wherein the polypeptide or compound containing a polypeptide portion is proinsulin, the polypeptide A chain of insulin, the polypeptide B chain of insulin, a growth hormone, an enzyme, an antibody, or the polypeptide portion of interferon.

6. A molecule useful as a cloning vehicle which includes a plasmid DNA and a promotor molecule in accordance with claim 1.

7. A molecule in accordance with claim 6 wherein the plasmid DNA is pBR322 DNA.

8. A molecule useful as a cloning vehicle which includes a phage DNA and a promoter molecule in accordance with claim 1.

9. A molecule in accordance with claim 7 wherein the phage DNA is λ phage DNA.

10. A molecule useful as a cloning vehicle which includes a viral DNA and a promoter molecule in accordance with claim 1.

11. A molecule useful as a cloning vehicle which includes a plasmid DNA and a molecule in accordance with claim 2.

12. A molecule useful as a cloning vehicle which includes a phage DNA and a molecule in accordance with claim 2.

13. A molecule useful as a cloning vehicle which includes a viral DNA and a molecule in accordance with claim 2.

14. A method of transforming *E. coli* which comprises transforming *E. coli* with a molecule in accordance with any of claims 6, 8, 10, 11, 12 or 13.

15. A method of inserting a double-stranded DNA gene into *E. coli*, said gene being associated with production of a desired chemical product, which comprises transforming *E. coli* with a molecule in accordance with claim 11.

16. A method of inserting a double-stranded DNA gene into *E. coli*, said gene being associated with production of a desired chemical product, which comprises transforming *E. coli* with a molecule in accordance with claim 12.

17. A method of inserting a double-stranded DNA gene into *E. coli*, said gene being associated with production of a desired chemical product, which comprises transforming *E. coli* with a molecule in accordance with claim 13.

18. An *E. coli* cell which includes a molecule in accordance with any of claims 1, 2, 6, 8, 10, 11, 12 or 13.

19. An *E. coli* cell which has been transformed in accordance with claim 14.

20. An *E. coli* cell into which a double-stranded DNA gene has been inserted in accordance with any of claims 15, 16 or 17.

21. A method of producing a desired chemical product which comprises cloning an *E. coli* cell in accordance with claim 20, said *E. coli* cell having therein the gene associated with production of said chemical product and said cloning being carried out under suitable conditions permitting expression of said gene and production of said product, and recovering the product so produced.

22. A method of enhanced production of proinsulin which comprises cloning an *E. coli* cell into which a DNA molecule has been inserted, said molecule including a promoter molecule in accordance with claim 1 and a DNA gene coding for production of proinsulin, said cloning being carried out under suitable conditions permitting enhanced expression of said proinsulin gene and enhanced production of proinsulin, and recovering the proinsulin so produced.

23. A method of enhanced production of the polypeptide A chain of insulin which comprises cloning an *E coli* cell into which a DNA molecule has been inserted, said molecule including a promoter molecule in accordance with claim 1 and a DNA gene coding for production of the polypeptide A chain of insulin, said cloning being carried out under suitable conditions permitting enhanced expression of said polypeptide A chain gene and enhanced production of polypeptide A chain, and recovering the A chain polypeptide so produced.

24. A method of enhanced production of the polypeptide B chain of insulin which comprises cloning an *E. coli* cell into which a DNA molecule has been inserted, said molecule including a promotor molecule in accordance with claim 1 and a DNA gene coding for production of the polypeptide B chain of insulin, said cloning being carried out under suitable conditions permitting enhanced expression of said polypeptide B chain gene and enhanced production of polypeptide B chain, and recovering the B chain polypeptide so produced.

25. A method of enhanced production of the polypeptide portion of interferon which comprises cloning an *E. coli* cell into which a DNA molecule has been inserted, said molecule including a promotor molecule in accordance with claim 1 and a DNA gene coding for production of the polypeptide portion of interferon, said cloning being carried out under suitable conditions permitting enhanced expression of said gene and enhanced production of the polypeptide portion of interferon, and recovering the interferon polypeptide so produced.

* * * * *